(12) United States Patent
Reisacher

(10) Patent No.: US 10,288,621 B2
(45) Date of Patent: *May 14, 2019

(54) METHODS FOR DETECTING ANTIBODIES IN MUCOSAL SAMPLES AND DEVICE FOR SAMPLING MUCOSAL MATERIAL

(71) Applicant: Cornell University, Ithaca, NY (US)

(72) Inventor: William Reisacher, New York, NY (US)

(73) Assignee: Cornell University, Ithaca, NY (US)

( * ) Notice: Subject to any disclaimer, the term of this patent is extended or adjusted under 35 U.S.C. 154(b) by 651 days.

This patent is subject to a terminal disclaimer.

(21) Appl. No.: 14/644,806

(22) Filed: Mar. 11, 2015

(65) Prior Publication Data
US 2015/0185228 A1 Jul. 2, 2015

Related U.S. Application Data

(63) Continuation of application No. 12/971,627, filed on Dec. 17, 2010, now Pat. No. 8,993,347.

(60) Provisional application No. 61/287,463, filed on Dec. 17, 2009.

(51) Int. Cl.
G01N 33/68 (2006.01)
A61B 10/02 (2006.01)

(52) U.S. Cl.
CPC ......... G01N 33/6854 (2013.01); A61B 10/02 (2013.01); A61B 2010/0208 (2013.01); A61B 2010/0216 (2013.01); G01N 2800/24 (2013.01)

(58) Field of Classification Search
None
See application file for complete search history.

(56) References Cited

U.S. PATENT DOCUMENTS

| | | | | |
|---|---|---|---|---|
| 6,051,226 A * | 4/2000 | Zavada | ................. | C07K 14/82 424/138.1 |
| 8,685,399 B2 * | 4/2014 | Hoff | ...................... | C07K 16/18 424/138.1 |
| 8,993,347 B2 * | 3/2015 | Reisacher | .......... | G01N 33/6854 436/518 |
| 2002/0006630 A1 * | 1/2002 | Sirbasku | .............. | A61K 31/138 435/7.23 |
| 2002/0147314 A1 * | 10/2002 | Briskin | ............ | C07K 14/70503 530/391.1 |
| 2003/0108965 A1 * | 6/2003 | Schummer | ........... | C07K 14/811 435/7.23 |
| 2005/0221305 A1 * | 10/2005 | Nelson | ................. | C12Q 1/6886 435/6.14 |
| 2006/0160762 A1 * | 7/2006 | Zetter | ................. | C12Q 1/6886 514/44 A |
| 2008/0214787 A1 * | 9/2008 | Zavada | ................. | C07K 14/82 530/387.3 |
| 2009/0029346 A1 * | 1/2009 | Millar | .................... | C12Q 1/708 435/5 |
| 2009/0047675 A1 * | 2/2009 | Roberts | ............. | C12N 15/1079 435/6.14 |
| 2009/0061454 A1 * | 3/2009 | Brody | ................... | C12Q 1/6886 435/6.14 |
| 2009/0239231 A1 * | 9/2009 | Adami | ................. | C12Q 1/6886 435/6.14 |
| 2009/0311664 A1 * | 12/2009 | Fong | ..................... | C12Q 1/6897 435/5 |
| 2010/0041013 A1 * | 2/2010 | Millar | .................. | C12Q 1/6883 435/5 |
| 2010/0086939 A1 * | 4/2010 | Kido | ................ | G01N 33/54373 435/7.1 |
| 2010/0240965 A1 * | 9/2010 | Furuta | ................. | A61K 31/437 600/300 |

* cited by examiner

Primary Examiner — Ann Y Lam
(74) Attorney, Agent, or Firm — Scully Scott Murphy & Presser

(57) ABSTRACT

A method to detect local antibodies such as antigen-specific IgE via a brush biopsy specimen of a mucosal surface of a subject is disclosed. The method is easily performed in an office setting on both adult and pediatric patients. Also disclosed is a brush device specially designed for harvesting materials from a mucosal surface such as the medial surface of the inferior turbinate.

10 Claims, 2 Drawing Sheets

NOSE AND NASAL CAVITIES

METHODS FOR DETECTING ANTIBODIES IN MUCOSAL SAMPLES AND DEVICE FOR SAMPLING MUCOSAL MATERIAL

CROSS-REFERENCE TO RELATED APPLICATION

This application is a continuation application of U.S. Ser. No. 12/971,627, filed Dec. 17, 2010, which claims the benefit of U.S. Provisional Application No. 61/287,463, filed Dec. 17, 2009, the contents of which are hereby incorporated by reference in its entirety.

BACKGROUND OF THE DISCLOSURE

Since the early 1970s, it has been known that antigen-specific IgE can be recovered from nasal and bronchial secretions in allergic patients who are challenged with that antigen (Yoshida T, 2005). It has also been demonstrated that IgE can be present in nasal secretions even though skin testing (Houri M, 1972) and in vitro testing (Stenius B, 1971) are negative, and it has been suggested that this locally produced IgE can cause an inflammatory reaction in a specific part of the airway, without affecting the rest of the body. In 1985, Ohashi et al. demonstrated elevated IgE levels in homogenized nasal mucosa from twelve patients with symptoms suggestive of allergy who were negative on skin and RAST testing (Ohashi Y, 1985).

Local IgE production has also been recognized in the pathogenesis of such conditions as allergic fungal rhinosinusitis (Pant H, 2009) and nasal polyposis (Sabirov A, 2008). Levels of *Alternaria*-specific IgE in nasal polyp tissue have been found to be significantly higher than non-polyp tissue from patients with chronic rhinosinusitis, and 60% of patients with nasal polyps had evidence of local IgE without evidence of *Alternaria*-specific IgE in the serum (Sabirov A, 2008). In addition, local IgE may also be responsible for symptoms in patients with chronic rhinitis who are diagnosed with "non-allergic rhinitis" based solely on negative skin and blood testing (Durham S R, 2000).

Current methods to collect local IgE in the nose include nasal lavage (Yoshida T, 2005) and surgical biopsy of nasal tissues (Ahn C N, 2009). However, nasal lavage is a difficult test to perform in the office setting, particularly in the pediatric population. In addition, it is uncomfortable for the patient and has a high rate of technical variability, which limits the interpretation of the results. Nasal lavage specimens can only collect IgE that is present in the mucus, but there is additional IgE present in the epithelium of the inferior turbinates (Ahn C N, 2009). Surgical biopsy will detect epithelial IgE, but this is an invasive test which is not practical in the office setting or ethical to perform solely for the purpose of allergy testing.

Brush biopsy with a cytology brush has been used inside the nose for the study of ciliary ultrastructure (Rutland J, 1982) and for viral culture (Winther B, 1986), but has not been used for collecting mucosal material and antibody testing.

SUMMARY OF THE DISCLOSURE

In one aspect, the instant disclosure is directed to a method of detecting local antibody molecules by obtaining a brush biopsy sample from a mucosal surface of a subject, and determining the presence of antibodies in the sample. In a specific embodiment, a brush biopsy specimen of the inferior turbinate is collected, which can be easily performed in the office setting on both adult and pediatric patients. Total IgEs or antigen-specific IgE can be detected in a collected brush biopsy specimen using standard methods.

In another embodiment, the instant disclosure provides a device designed for collecting a brush biopsy sample from a mucosal surface of a subject.

DETAILED DESCRIPTION OF THE DISCLOSURE

Figure 1:
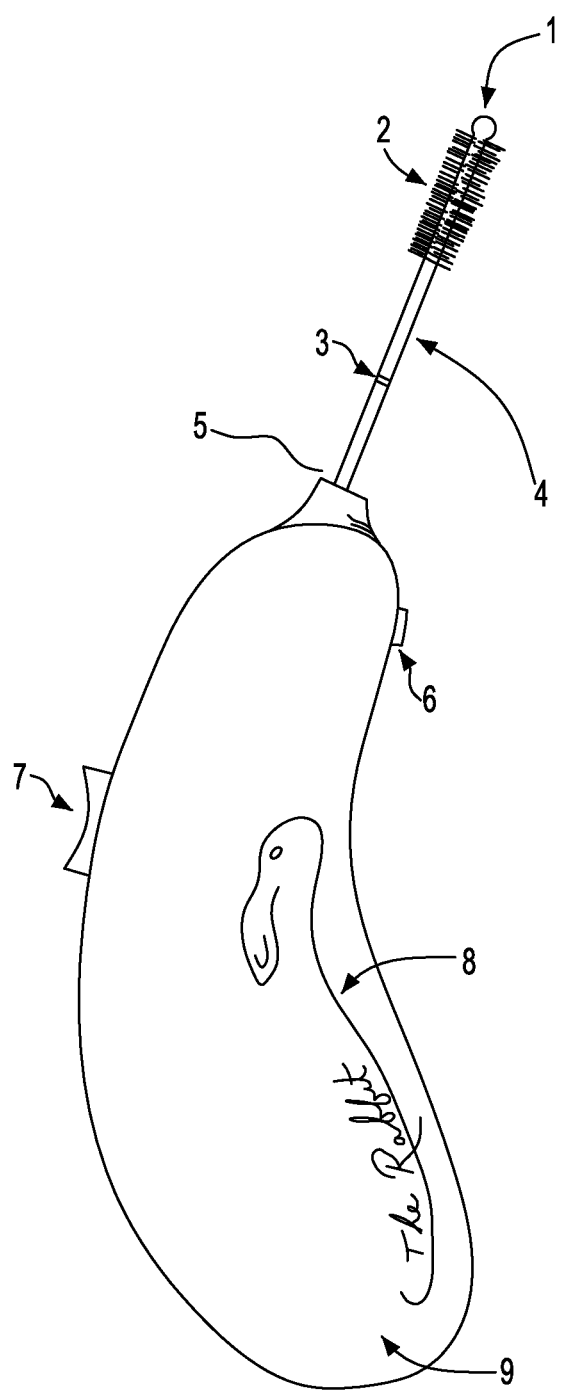
FIG. 1. A specific embodiment of the device disclosed herein for retrieving a brush biopsy sample from medial surface of the inferior turbinate.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

It has been recognized in accordance with the instant disclosure that a brush biopsy sample can be effectively retrieved from a mucosal surface (such as the inferior nasal concha) for detecting local antibody molecules, and the antibody molecules detected can be used in diagnosis of various conditions and disorders. Accordingly, this disclosure provides methods for detecting local antibodies in a brush biopsy sample as well as devices for retrieving a brush biopsy sample.

In one aspect, the instant disclosure is directed to a method of detecting local antibody molecules by obtaining a brush biopsy sample from a mucosal surface of a subject, and determining the presence of antibodies in the sample.

By a "mucosa," it is meant a membrane that constitutes the surface lining of body cavities/orifices, respiratory and gastrointestinal tracts, internal organs and other body parts, and is typically covered with epithelial cells. An orifice is an opening of a body and includes, for example, the ear, the nose, the mouth, the urethral orifice, and the anus. Thus, a mucosal surface can be, for example, the inner surface of the nose, mouth, throat, esophagus, the stomach, the small intestine, the large intestine, the rectum, the urethra, vagina, uterus, or cervix, as well as the surface of the tongue or adenoids, the prepuce, and glans.

By a "subject," it is meant an individual mammal. In some embodiments, the mammal is a human, a primate, a domestic cat, a domestic dog, a cow, a sheep, a goat, a pig, a rat, or a mouse.

The term "local antibodies" is used to refer antibodies present in certain tissues or parts of a body that do not necessarily circulate through the blood and spread to other tissues or parts of the body, as opposed to antibodies present in the blood (or "systemic antibodies").

As disclosed herein, to achieve detection of local antibodies at a mucosal surface, a brush biopsy sample is obtained from the mucosal surface. For example, a biopsy brush is inserted into an orifice of a subject so that the biopsy brush contacts a mucosal surface in the orifice, and the brush is manipulated, e.g., being applied with an appropriate amount of pressure or rotated against the mucosal surface, so that sufficient mucosal materials becomes associated with the biopsy brush, and removed from the orifice of the subject.

It has been established in this disclosure that adequate mucosal material can be obtained by brush biopsy, which is believed to contain both mucosal secretions and cellular materials including epithelial cells of the mucosa. As disclosed herein, such brush biopsy sample can be released from the brush (e.g., by washing or immersing the brush with suitable solutions such as a saline solution), and then used in detecting the presence and/or amount of antibody molecules (immunoglobulins) in the sample.

Detection can be directed to the entire population of immunoglobulins in the sample, or to immunoglobulins of particular isotypes. In some embodiments, detection is directed to the IgA, IgD, IgE, IgG, and IgM, which are the immunoglobulin isotypes in humans. In other embodiments where the subject being tested is a mammal other than human, detection is directed to immunoglobulin isotypes of other mammals. In some embodiments, the immunoglobulins are of particular immunoglobulin isotype subclasses, for example, IgG1, IgG2, IgG3, IgG4, IgA1, and IgA2, which are the immunoglobulin isotypes in humans. In other embodiments, the immunoglobulin isotype classes are the isotype classes of other mammals.

In some embodiments, total antibody molecules in a biopsy sample are detected irrespective antigen specificity. In other embodiments, antigen-specific antibody molecules of all types (i.e., all isotypes and subclasses) or of particular isotype or subclass are being detected.

In specific embodiments, the antigen is an allergen. By "allergen," it is meant a molecule that is capable of inducing an allergic response in a subject. The detection method disclosed herein is capable of detecting antibodies against various allergens. In some embodiments, the allergen derives from a plant (a "plant allergen"). In specific embodiments, the allergens derive from the White Oak tree (*Quercus alba*), Timothy Grass (*Phleum pratense*), ragweeds (*Ambrosia* spp., e.g., *Ambrosia artemisilfolia*). A plant allergen can derive from various parts of a plant, for example, the pollen of the plant. In other embodiments, the allergen is a microbial allergen, such as *Alternaria* spp. (e.g., *Alternaria alternata*), and *Aspergillus* spp. (e.g., *Aspergillus fumigata*). In some other embodiments, the allergens derive from animals, such as domestic cat, dog, house dust mites (*Dermatophagoides* spp.), and cockroaches (animals of the order Blattaria). In additional embodiments, the allergen derives from food, e.g., milk, eggs, peanuts, tree nuts, seafood, shellfish, soy, rice, and wheat.

In other embodiments, the antigens can be specific molecules, such as DerP1, FelD1 and the like.

Antibodies, both total antibodies and antigen-specific antibodies, can be detected using assays and techniques known in the art. Suitable assays include direct immunofluorescence, indirect immunofluorescence, radioimmunoassay, enzyme-linked immunosorbent assay (ELISA), immunoprecipitation, Western blotting, isoelectric focusing, immunoelectrophoresis, radial immunodiffusion, flow cytometry, surface plasmon resonance, or bioassay. In some embodiments, the assay is a capture or "sandwich" ELISA. In other embodiments, the assay is an ImmunoCAP® assay. The basis of the ImmunoCAP® technology is a 3 dimensional cellulose polymer in a plastic reserve. This provides high binding capacity of allergen proteins, including those present in very low levels, providing increased sensitivity, specificity, and reproducibility. The commercial source of this immunofluorescence assay is Phadia (Portage, Mich.).

Figure 2:
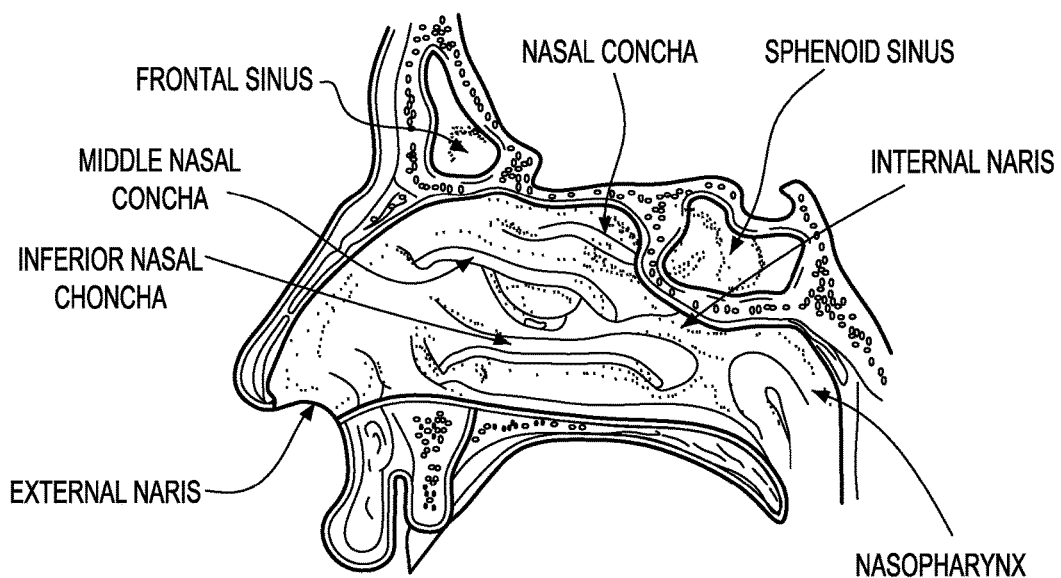
FIG. 2. Anatomy of the nose.

In an exemplary embodiment, a method is disclosed that effectively detects local IgE in nasal mucosa. More specifically, a brush biopsy sample is retrieved from the inferior turbinate, also known as inferior nasal concha (see FIG. 2), and the sample is used to detect IgE, either total IgE or antigen-specific IgE. The level of IgE detected can be compared to a reference value as a basis of diagnosis (e.g., diagnosis of allergy). IgE testing using brush biopsy samples has been found herein to generally correlate with results from skin prick testing. Prior to this disclosure, brush biopsy has not been proposed for collecting mucosal material and detecting local IgEs in connection with diagnosis of allergies.

In a further aspect, the instant disclosure provides a device designed for collecting a brush biopsy sample from a mucosal surface of a subject.

One device disclosed herein is named The RABBIT (Rotating Automatic Brush Biopsy of the Inferior Turbinate), an exemplary configuration of which is depicted in FIG. 1. Such device provides an easy, quick, inexpensive and non-invasive method for brush biopsy of the nose. Standard cytology brushes, which are used most commonly for cervical biopsy, are too long for safe, day to day clinical use in the nose. They often contain metal components which may damage delicate tissues in the nose and are difficult to use quickly enough in the pediatric population to obtain an adequate sample of epithelial cells.

The device (8) is designed to fit comfortably in the hand and weighs less than 1 pound. The shell of the device (9), preferably plastic, is approximately 16×5×2 cm in dimension, and houses a motor or motors for moving the shaft and brush (4). The motor or motors may be powered by an electric cord, and/or by a battery that may also be inside the shell; the battery may be rechargeable. The motor or motors may be turned on and off by a switch (7) or switches. The motor or motors may cause the shaft and brush to rotate, they may also cause the shaft and brush to move axially. The switch (7) or switches may also control the axial movement, or said axial movement may be automatic. The shaft and brush (4) enters the shell through a housing (5), and may be of a single piece with the motor, in an embodiment in which the entire device is either intended for single use and disposed or is made to be sterilized, or may be removable. If the shaft and brush are removable, a quick release switch (6) or other actuator for quick switching may be located on the outside of the shell. The shaft and brush (4) may be approximately 7 cm in length, and may be made of any suitably stiff yet pliable material such as plastic. In a preferred embodiment, the shaft terminates with an atraumatic structure (1) such as a rubber ring or non-latex foam tip. A shorter shaft/brush may be employed for pediatric patients. The shaft may have markings (3) indicating the maximum depth to which the brush should be inserted into the nose. The brushing elements (2) are disposed on the shaft for a length of 1-2 cm, and may extend 1-2 mm radially outward from the shaft. Brushing elements (2) may be bristles, (as shown in FIG. 1) loops, ridges, corrugations, or alternatively, any scraping collection device. Brushing elements may be made from known material and fixedly attached to the surface of the shaft or, alternatively, they may be inherently formed on the surface of the shaft.

Modifications to the device shown in FIG. 1 can be made to adapt the device for retrieving biopsy samples from a particular mucosal surface. For example, the length and material of the shaft can be selected to make the brush move easily and flexibly through the GI tract and retrieve materials from a particular site in the GI tract.

The methods and the devices disclosed herein are useful for diagnosing disease and conditions associated with or characterized by abnormal levels of antibodies, particularly abnormal levels of local antibody levels. By "abnormal" it is meant that the level of antibodies in a patient having a disease or condition is significantly increased or decreased as compared to normal, healthy subjects. Conditions suitable for diagnosis in accordance with the methods and devices disclosed herein include allergy, allergic fungal rhinosinusitis, nasal polyposis or non-allergic rhinitis. The instant methods and devices are particularly useful for diagnosing allergies, including seasonal and food allergies, allergies to any allergens such as those described above. The methods and devices disclosed herein provide a convenient alternative to standard allergy testing in both the pediatric and adult populations.

Examples

The present description is further illustrated by the following examples, which should not be construed as limiting in any way. The contents of all cited references (including literature references, issued patents, and published patent applications as cited throughout this application) are hereby expressly incorporated by reference.

Brush biopsy was performed in the outpatient setting. After informed consent was obtained, the nose was decongested and anesthetized with topical 2% lidocaine and 1% phenylephrine. After 5 minutes, a standard cytology brush was inserted along the medial aspect of the anterior ⅓ of the inferior turbinate on the side of the more patent nostril. The brush was rotated back and forth several times, while avoiding direct pressure on the septum.

After the brush was withdrawn, it was immersed in a 12×75 mm round bottom polypropylene tube containing 1 cc of PBS. The brush was rotated for 1 minute and then irrigated with 1 cc of additional PBS to release all mucus and cells bound to the bristles, and the specimen was stored at −20° C. Prior to freezing, 0.5 cc of the PBS was set aside for BCA protein assay to determine total protein level.

Specimens were sent to a reference laboratory (IBT Laboratories, Lenexa, Kans.) for ImmunoCAP® analysis to determine total IgE level as well as antigen-specific IgE levels for the nine selected antigens. Specimens were standardized for total protein.

The population chosen for this study was approximately 20 human patients, 18 years of age or older, who demonstrated at least 1 positive reaction (wheal >3 mm or 2 mm greater than the negative control) on skin prick testing using a battery of 9 inhalant allergens: White Oak, Timothy grass, Ragweed, Cat dander, Dog dander, Cockroach, *Alternaria*, *Aspergillus*, and *Dermatophagoides farinae*. Patients who had immunotherapy in the past were excluded from participation in this study.

Nine of the twenty patients were subjected to a further study which compared brush biopsy of the inferior turbinate with skin prick testing for the overall detection of antigen-specific IgE and the detection of individual antigens.

Each subject tested positive to one or more of the following antigens on skin prick testing ("SPT"): White Oak, Timothy Grass, Ragweed, Cat, Dog, Cockroach, *Alternaria*, *Aspergillus* (2 molds) and *D. Farinae* (house dust mite). Each patient underwent Brush Biopsy Testing ("BBT") as described above. The brush biopsy samples obtained from the patients were analyzed by ImmunoCAP® and antigen-specific IgE responses were assessed. A brush biopsy sample having an IgE level equal to or above 0.10 kU/L for an allergen was scored "positive" for that allergen whereas a brush biopsy sample having an IgE level less than 0.10 kU/L for an allergen was scored "negative" for that allergen. The "class" of response was also determined based on the level of antigen-specific IgE detected. A higher "class" number indicates higher levels of IgE (Table 11).

TABLE 1

Results for Subject 1, a forty year-old female

| Test | Result | Flag/Class | Units | Reference Ranges |
|---|---|---|---|---|
| Immunoglobulin E (IgE) ImmunoCAP | 6 | | IU/mL | 5-79 |
| Cat Dander IgE | 0.60 | 1 | kU/L | <0.35 |
| Dog Dander IgE | 0.21 | 0/1 | kU/L | <0.35 |
| Timothy Grass (*Phleum pratense*) IgE | <0.10 | 0 | kU/L | <0.35 |
| Ragweed Short/Common (*Ambrosia artemisilfolia*) IgE | <0.10 | 0 | kU/L | <0.35 |
| Oak White (*Quercus alba*) IgE | 0.18 | 0/1 | kU/L | <0.35 |
| *Alternaria tenuis/alternata* IgE | <0.10 | 0 | kU/L | <0.35 |
| *Aspergillus fumigatus* IgE | <0.10 | 0 | kU/L | <0.35 |
| Mite *Dermatophagoides farinae* IgE | 0.10 | 0/1 | kU/L | <0.35 |
| Cockroach German (*Blatella germanica*) IgE | 0.14 | 0/1 | kU/L | <0.35 |

TABLE 2

Results for Subject 2, a thirty year-old female

| Test | Result | Flag/Class | Units | Reference Ranges |
|---|---|---|---|---|
| Immunoglobulin E (IgE) ImmunoCAP | 12 | | IU/mL | 4-59 |
| Cat Dander IgE | 1.40 | 2 | kU/L | <0.35 |
| Dog Dander IgE | 1.15 | 2 | kU/L | <0.35 |
| Timothy Grass (*Phleum pratense*) IgE | <0.10 | 0 | kU/L | <0.35 |
| Ragweed Short/Common (*Ambrosia artemisilfolia*) IgE | 0.11 | 0/1 | kU/L | <0.35 |
| Oak White (*Quercus alba*) IgE | 0.21 | 0/1 | kU/L | <0.35 |
| *Alternaria tenuis/alternata* IgE | 0.11 | 0/1 | kU/L | <0.35 |
| *Aspergillus fumigatus* IgE | <0.10 | 0 | kU/L | <0.35 |
| Mite *Dermatophagoides farinae* IgE | 0.12 | 0/1 | kU/L | <0.35 |
| Cockroach German (*Blatella germanica*) IgE | 0.14 | 0/1 | kU/L | <0.35 |

TABLE 3

Results for Subject 3, a twenty-eight year-old male

| Test | Result | Flag/Class | Units | Reference Ranges |
|---|---|---|---|---|
| Immunoglobulin E (IgE) ImmunoCAP | 6 | | IU/mL | 4-59 |
| Cat Dander IgE | 0.20 | 0/1 | kU/L | <0.35 |
| Dog Dander IgE | 0.11 | 0/1 | kU/L | <0.35 |
| Timothy Grass (*Phleum pratense*) IgE | 0.18 | 0/1 | kU/L | <0.35 |
| Ragweed Short/Common (*Ambrosia artemisilfolia*) IgE | 0.47 | 1 | kU/L | <0.35 |

TABLE 3-continued

Results for Subject 3, a twenty-eight year-old male

| Test | Result | Flag/Class | Units | Reference Ranges |
|---|---|---|---|---|
| Oak White (*Quercus alba*) IgE | 0.21 | 0/1 | kU/L | <0.35 |
| *Alternaria tenuis/alternata* IgE | <0.10 | 0 | kU/L | <0.35 |
| *Aspergillus fumigatus* IgE | <0.10 | 0 | kU/L | <0.35 |
| Mite *Dermatophagoides farinae* IgE | 0.10 | 0/1 | kU/L | <0.35 |
| Cockroach German (*Blatella germanica*) IgE | 0.13 | 0/1 | kU/L | <0.35 |

TABLE 4

Results for Subject 4, a twenty-nine year-old female

| Test | Result | Flag/Class | Units | Reference Ranges |
|---|---|---|---|---|
| Immunoglobulin E (IgE) ImmunoCAP | 6 | | IU/mL | 4-59 |
| Cat Dander IgE | 0.23 | 0/1 | kU/L | <0.35 |
| Dog Dander IgE | 0.17 | 0/1 | kU/L | <0.35 |
| Timothy Grass (*Phleum pratense*) IgE | <0.10 | 0 | kU/L | <0.35 |
| Ragweed Short/Common (*Ambrosia artemisilfolia*) IgE | 0.11 | 0/1 | kU/L | <0.35 |
| Oak White (*Quercus alba*) IgE | 0.16 | 0/1 | kU/L | <0.35 |
| *Alternaria tenuis/altenata* IgE | 0.11 | 0/1 | kU/L | <0.35 |
| *Aspergillus fumigatus* IgE | <0.10 | 0 | kU/L | <0.35 |
| Mite *Dermatophagoides farinae* IgE | 0.11 | 0/1 | kU/L | <0.35 |
| Cockroach German (*Blatella germanica*) IgE | 0.14 | 0/1 | kU/L | <0.35 |

TABLE 5

Results for Subject 5, a twenty-seven year-old male

| Test | Result | Flag/Class | Units | Reference Ranges |
|---|---|---|---|---|
| Immunoglobulin E (IgE) ImmunoCAP | 4 | | IU/mL | 4-59 |
| Cat Dander IgE | <0.10 | 0 | kU/L | <0.35 |
| Dog Dander IgE | <0.10 | 0 | kU/L | <0.35 |
| Timothy Grass (*Phleum pratense*) IgE | <0.10 | 0 | kU/L | <0.35 |
| Ragweed Short/Common (*Ambrosia artemisilfolia*) IgE | <0.10 | 0 | kU/L | <0.35 |
| Oak White (*Quercus alba*) IgE | 0.18 | 0/1 | kU/L | <0.35 |
| *Alternaria tenuis/alternata* IgE | <0.10 | 0 | kU/L | <0.35 |
| *Aspergillus fumigatus* IgE | <0.10 | 0 | kU/L | <0.35 |
| Mite *Dermatophagoides farinae* IgE | 0.47 | 1 | kU/L | <0.35 |
| Cockroach German (*Blatella germanica*) IgE | 0.13 | 0/1 | kU/L | <0.35 |

TABLE 6

Results for Subject 6, a twenty-five year-old male

| Test | Result | Flag/Class | Units | Reference Ranges |
|---|---|---|---|---|
| Immunoglobulin E (IgE) ImmunoCAP | 32 | | IU/mL | 4-59 |
| Cat Dander IgE | 2.73 | 2 | kU/L | <0.35 |
| Dog Dander IgE | 0.68 | 1 | kU/L | <0.35 |
| Timothy Grass (*Phleum pratense*) IgE | 0.15 | 0/1 | kU/L | <0.35 |
| Ragweed Short/Common (*Ambrosia artemisilfolia*) IgE | <0.10 | 0 | kU/L | <0.35 |
| Oak White (*Quercus alba*) IgE | 5.43 | 3 | kU/L | <0.35 |
| *Alternaria tenuis/alternata* IgE | 0.13 | 0/1 | kU/L | <0.35 |
| *Aspergillus furmigatus* IgE | <0.10 | 0 | kU/L | <0.35 |
| Mite *Dermatophagoides farinae* IgE | 3.14 | 2 | kU/L | <0.35 |
| Cockroach German (*Blatella germanica*) IgE | 0.16 | 0/1 | kU/L | <0.35 |

TABLE 7

Results for Subject 7, a thirty-six year-old male

| Test | Result | Flag/Class | Units | Reference Ranges |
|---|---|---|---|---|
| Immunoglobulin E (IgE) ImmunoCAP | 6 | | IU/mL | 5-79 |
| Cat Dander IgE | 0.10 | 0/1 | kU/L | <0.35 |
| Dog Dander IgE | 0.10 | 0/1 | kU/L | <0.35 |
| Timothy Grass (*Phleum pratense*) IgE | 1.13 | 2 | kU/L | <0.35 |
| Ragweed Short/Common (*Ambrosia artemisilfolia*) IgE | <0.10 | 0 | kU/L | <0.35 |
| Oak White (*Quercus alba*) IgE | 0.18 | 0/1 | kU/L | <0.35 |
| *Alternaria tenuis/alternata* IgE | <0.10 | 0 | kU/L | <0.35 |
| *Aspergillus fumigatus* IgE | 0.10 | 0/1 | kU/L | <0.35 |
| Mite *Dermatophagoides farinae* IgE | 0.12 | 0/1 | kU/L | <0.35 |
| Cockroach German (*Blatella germanica*) IgE | 0.13 | 0/1 | kU/L | <0.35 |

TABLE 8

Results for Subject 8, a twenty-four year-old female

| Test | Result | Flag/Class | Units | Reference Ranges |
|---|---|---|---|---|
| Immunoglobulin E (IgE) ImmunoCAP | 18 | | IU/mL | 4-59 |
| Cat Dander IgE | 0.46 | 1 | kU/L | <0.35 |
| Dog Dander IgE | 0.44 | 1 | kU/L | <0.35 |
| Timothy Grass (*Phleum pratense*) IgE | 1.57 | 2 | kU/L | <0.35 |
| Ragweed Short/Common (*Ambrosia artemisilfolia*) IgE | 0.13 | 0/1 | kU/L | <0.35 |
| Oak White (*Quercus alba*) IgE | 2.12 | 2 | kU/L | <0.35 |
| *Alternaria tenuis/alternata* IgE | 0.15 | 0/1 | kU/L | <0.35 |
| *Aspergillus fumigatus* IgE | 0.10 | 0/1 | kU/L | <0.35 |
| Mite *Dermatophagoides farinae* IgE | 1.10 | 2 | kU/L | <0.35 |
| Cockroach German (*Blatella germanica*) IgE | 0.18 | 0/1 | kU/L | <0.35 |

TABLE 9

Results for Subject 9, a fifty-four year-old female

| Test | Result | Flag/Class | Units | Reference Ranges |
|---|---|---|---|---|
| Immunoglobulin E (IgE) ImmunoCAP | 3 | | IU/mL | 3-48 |
| Cat Dander IgE | 0.10 | 0/1 | kU/L | <0.35 |
| Dog Dander IgE | <0.10 | 0 | kU/L | <0.35 |
| Timothy Grass (*Phleum pratense*) IgE | <0.10 | 0 | kU/L | <0.35 |

TABLE 9-continued

Results for Subject 9, a fifty-four year-old female

| Test | Result | Flag/Class | Units | Reference Ranges |
|---|---|---|---|---|
| Ragweed Short/Common (*Ambrosia artemisilfolia*) IgE | 0.12 | 0/1 | kU/L | <0.35 |
| Oak White (*Quercus alba*) IgE | 0.17 | 0/1 | kU/L | <0.35 |
| *Alternaria tenuis/alternata* IgE | <0.10 | 0 | kU/L | <0.35 |
| *Aspergillus fumigatus* IgE | <0.10 | 0 | kU/L | <0.35 |
| Mite *Dermatophagoides farinae* IgE | <0.10 | 0 | kU/L | <0.35 |
| Cockroach German (*Blatella germanica*) IgE | 0.15 | 0/1 | kU/L | <0.35 |

TABLE 10

Comparison of Brush Biopsy Testing with Skin Prick Testing for subjects 1-9. "Concordance" indicates the combined proportion of allergens detected that were BBT+/SPT+ and BBT−/SPT−.

| Subject | BBT+/SPT+ | BBT−/SPT− | BBT−/SPT+ | BBT+/SPT− | Concordance |
|---|---|---|---|---|---|
| 1 | 3 | 0 | 4 | 2 | 3/9 |
| 2 | 3 | 1 | 1 | 4 | 4/9 |
| 3 | 5 | 2 | 0 | 2 | 7/9 |
| 4 | 2 | 2 | 0 | 5 | 4/9 |
| 5 | 1 | 5 | 1 | 2 | 6/9 |
| 6 | 5 | 2 | 0 | 2 | 7/9 |
| 7 | 2 | 1 | 1 | 5 | 3/9 |
| 8 | 3 | 0 | 0 | 6 | 3/9 |
| 9 | 4 | 2 | 3 | 0 | 6/9 |
| Total | 28 | 15 | 10 | 28 | 43/81 |
| Percentage | 34.60% | 18.50% | 12.30% | 34.60% | 53.10% |

TABLE 11

Comparison of Brush Biopsy Testing with Skin Prick Testing by allergen tested. "Concordance" indicates the combined proportion of allergens detected that were BBT+/SPT+ and BBT−/SPT−.

| Antigen (IgE) | BBT+/SPT+ | BBT−/SPT− | BBT−/SPT+ | BBT+/SPT− | Concordance |
|---|---|---|---|---|---|
| White Oak | 6 | 0 | 3 | 0 | 6/9 |
| Timothy Grass | 4 | 2 | 1 | 2 | 6/9 |
| Ragweed short/common | 3 | 2 | 2 | 2 | 5/9 |
| Cat Dander | 5 | 1 | 3 | 0 | 5/9 |
| Dog | 0 | 0 | 7 | 2 | 2/9 |
| Cockroach | 5 | 0 | 4 | 0 | 5/9 |
| *Alternaria* | 1 | 1 | 3 | 4 | 5/9 |
| *Aspergillus* | 1 | 2 | 1 | 5 | 6/9 |
| *D. Farinae* | 4 | 1 | 4 | 0 | 4/9 |

TABLE 12

Results of Brush Biopsy Testing by Level of Response (Class).

| Class | Range of Responses (kU/L) | Total number of patients in grade |
|---|---|---|
| 0 | 0-0.1 | 25 |
| 0 or 1 | 0.1-0.35 | 41 |
| 1 (low) | 0.35-0.7 | 6 |
| 2 (medium) | 0.71-3.5 | 8 |
| 3 (high) | 3.51-17.5 | 1 |
| Total | | 81 |

TABLE 13

Total Number of Positive Tests.

| | SPT | BBT |
|---|---|---|
| Number of positive tests | 38 | 56 |

REFERENCES

Yoshida T, Usui A, Kusumi T, et al. A quantitative analysis of cedar pollen-specific immunoglobulins in nasal lavage supported the local production of specific IgE, not of specific IgG. Microbiol Immunol 2005; 49(6):529-534.

Houri M, Mayer A L R, Houghton L E and Jacobs D. Correlation of skin, nasal and inhalation tests with the IgE in serum, nasal fluid and sputum. Clinical Allergy 1972; 2:285-298.

Stenius B, Wide L, Seymour W M et al. Clinical significance of specific IgE to common allergens. I. Relationship of specific IgE against *Dermatophagoides* spp. And grass pollen to skin and nasal tests and history. Clinical Allergy 1971; 1:37.

Ohashi Y, Nakai Y, Kuroki K, et al. Topical immunology of nasal allergy and mucosal IgE antibodies. Arch Otorhinolaryngol 1985; 241:169-174.

Pant H, Schembri M A, Wormald P J and Macardle P J. IgE-mediated fungal allergy in allergic fungal sinusitis. Laryngoscope 2009; 119:1046-1052.

Sabirov A, Hamilton R G, Jacobs J B, et al. Role of local immunoglobulin E specific for *Alternaria alternata* in the pathogenesis of nasal polyposis. Laryngoscope 2008; 118:4-9.

Durham S R, Smurthwaite L, Gould H J. Local IgE production. Am J Rhinol 2000; 14:305-357.

Ahn C N, Wise S K, Lather D M R et al. Local production of antigen-specific IgE in different anatomic subsites of allergic fungal rhinosinusitis patients. Otolaryngol Head Neck Surg 2009; 141:97-103.

Rutland J, Dewar A, Cox T and Cole P. Nasal brushing for the study of ciliary ultrastructure. J Clin Pathol 1982; 35(3):357-9.

Winther B, Gwaltney J M, Mygind N, et al. Sites of rhinovirus recovery after point inoculation of the upper airway. JAMA 1986; 256(13):1763-1767.

What is claimed is:

1. A method for detecting local antibody molecules at a mucosal surface in a subject, comprising:
   i) obtaining a brush biopsy sample from the mucosal surface; and
   ii) detecting the presence of antibody molecules in said sample.

2. The method of claim 1, wherein the sample is obtained from a mucosal surface of an orifice, or a mucosal surface of the respiratory and gastrointestinal tracts.

3. The method of claim 2, wherein the orifice is selected from the mouth, nose or ear.

4. The method of claim 2, wherein the sample is obtained from a mucosal surface of the throat, esophagus or stomach.

5. The method of claim 1, wherein the sample is obtained from a mucosal surface of the inferior turbinate.

6. The method of claim 1, wherein said antibody is selected from the group consisting of IgA, IgD, IgG, and IgM.

7. The method of claim 6, wherein said antibody is specific to an antigen.

8. The method of claim 7, wherein said antigen is an allergen.

9. The method of claim 7, further comprising measuring the level of IgE specific to at least one antigen.

10. The method of claim 6, further comprising measuring the level of total IgE.

* * * * *